US009510775B2

(12) United States Patent
Morren et al.

(10) Patent No.: US 9,510,775 B2
(45) Date of Patent: Dec. 6, 2016

(54) MOTION DETERMINATION APPARATUS

(75) Inventors: Geert Guy Georges Morren, Tienen (BE); Anmin Jin, Eindhoven (NL); Bin Jin, Eindhoven (NL); Haris Duric, Eindhoven (NL); Ronaldus Maria Aarts, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 936 days.

(21) Appl. No.: 13/320,029

(22) PCT Filed: Jun. 2, 2010

(86) PCT No.: PCT/IB2010/052466
§ 371 (c)(1),
(2), (4) Date: Nov. 11, 2011

(87) PCT Pub. No.: WO2010/140130
PCT Pub. Date: Dec. 9, 2010

(65) Prior Publication Data
US 2012/0065524 A1  Mar. 15, 2012

(30) Foreign Application Priority Data
Jun. 5, 2009 (EP) .................................... 09162004

(51) Int. Cl.
*A61B 5/08* (2006.01)
*A61B 5/11* (2006.01)
*A61B 5/113* (2006.01)

(52) U.S. Cl.
CPC ............ *A61B 5/1102* (2013.01); *A61B 5/1135* (2013.01); *A61B 2562/0219* (2013.01)

(58) Field of Classification Search
USPC ....................................................... 600/484
See application file for complete search history.

(56) References Cited

U.S. PATENT DOCUMENTS 7,827,011 B2* 11/2010 DeVaul et al. ................ 702/190
8,103,304 B1*  1/2012 Miller ............... H04M 1/72569
                                                        455/550.1

(Continued)

FOREIGN PATENT DOCUMENTS

JP      200534364       2/2005
JP      2006320734 A    11/2006
WO      2004043263 A2   5/2004
WO      2005048824 A2   6/2005

OTHER PUBLICATIONS

Estimation of respiratory waveform and heart rate using an accelerometer, D. H. Phan.*

(Continued)

*Primary Examiner* — Michael Kahelin
*Assistant Examiner* — Mitchell E Alter (57) ABSTRACT

The invention relates to a motion determination apparatus for determining motion of a moving object, wherein the motion determination apparatus (1) comprises a multi-axial accelerometer (2) for being positioned at the moving object (4), wherein the multi-axial accelerometer (2) is adapted to generate accelerometer signals indicative of the acceleration along different spatial axes. The motion determination apparatus further comprises a motion signal generation unit (3) for generating a motion signal indicative of the motion of the object (4) by combining the accelerometer signals of different spatial axes. The combination of the accelerometer signals of different spatial axes yields a motion signal having a large signal-to-noise ratio, even if an axis is located close to a rotational axis of the movement.

14 Claims, 6 Drawing Sheets

(56) References Cited

U.S. PATENT DOCUMENTS

| | | | |
|---|---|---|---|
| 2004/0039420 A1 | 2/2004 | Jayne et al. | |
| 2006/0135883 A1* | 6/2006 | Jonsson et al. | 600/546 |
| 2006/0253043 A1* | 11/2006 | Zhang et al. | 600/512 |
| 2007/0032749 A1* | 2/2007 | Overall | A61B 5/02444 600/595 |
| 2007/0123806 A1* | 5/2007 | Bouvier | A43D 1/02 600/595 |
| 2007/0293781 A1* | 12/2007 | Sims et al. | 600/534 |
| 2008/0162088 A1* | 7/2008 | DeVaul et al. | 702/190 |
| 2009/0062628 A1* | 3/2009 | Yamamoto et al. | 600/301 |

OTHER PUBLICATIONS

Estimation of Respiratory Waveform Using an Accelerometer, P.D. Hung.*

Hong, J., et al, Classification Technique of Human Motion Context based on Wireless Sensor Network, Proceedings of the 2005 IEEE Engineering in Medicine and Biology 27th Annual Conference Shanghai, China, Sep. 1-4, 2005.*

Luinge H. et al, Inclination Measurement of Human Movement Using a 3-D Accelerometer With Autocalibration vol. 12, No. 1, Mar. 2004.*

Torres, Abel, et al. "Application of the empirical mode decomposition method to the analysis of respiratory mechanomyographic signals." Engineering in Medicine and Biology Society, 2007. EMBS 2007. 29th Annual International Conference of the IEEE. IEEE, 2007 (Torres).*

S. M. Holland "Principal Components Analysis (PCA)" Department of Geology, University of Georgia, Athens, GA 30602-2501 May 2008 (Holland).*

Belouchrani, A., et al.; A Blind source Separation Technique Using Second-Order Statistics; 1997; IEEE Trans. on Signal Processing; 45(2)434-444.

* cited by examiner

MOTION DETERMINATION APPARATUS

FIELD OF THE INVENTION

The invention relates to a motion determination apparatus and method for determining motion of a moving object. The invention relates further to a corresponding computer program.

BACKGROUND OF THE INVENTION

US 2005/0277842 discloses a monitor respiration movement device to be used on humans and also on animals for controlling respiration movements and specially to control the apnea periods on infants. The device comprises an accelerometer and a micro controller, wherein the accelerometer includes a motion detector and a plurality of output plugs and wherein the micro controller includes a plurality of input sockets. The plurality of output plugs is connected to the plurality of input sockets and the micro controller includes signal outputs which are connected to an alarm means.

SUMMARY OF THE INVENTION

The monitor respiration movement device disclosed in US 2005/0277842 relies on an accelerometer signal along a single spatial axis. Since respiration-related changes in the accelerometer signal are caused by orientation changes with respect to gravity, a problem occurs when the orientation of the spatial single axis with respect to gravity does not change due to respiration because in this case the respiration can not be monitored using the single axis. This can happen, for example, if the respiration-induced movement is a rotation around the spatial single axis itself irrespective of its orientation with respect to gravity. Moreover, if the respiration-induced movement is a rotation around a rotational axis being close to the spatial single axis of the accelerometer, only a small accelerometer signal with a low signal-to-noise ratio is measured. This reduces the quality of the accelerometer signal caused by respiration.

It is an object of the present invention to provide a motion determination apparatus and a method for determining motion of a moving object, wherein a motion signal indicative of the motion is generated by using an accelerometer and wherein the quality of the motion signal is improved.

In a first aspect of the present inventions a motion determination apparatus for determining motion of a moving object is presented, wherein the motion determination apparatus comprises:

a multi-axial accelerometer for being positioned at the moving object, wherein the multi-axial accelerometer is adapted to generate accelerometer signals indicative of the acceleration along different spatial axes, a motion signal generation unit for generating a motion signal indicative of the motion of the object by combining the accelerometer signals of different spatial axes.

Since the accelerometer is a multi-axial accelerometer, a movement being a rotation around one of the axes of the multi-axial accelerometer yields a change in the accelerometer signal of another one of the axes of the multi-axial accelerometer. Thus, the combination of the accelerometer signals of different spatial axes yields a motion signal being large and having a large signal-to-noise ratio, even if an axis is located close to a rotational axis of a movement which should be detected by the multi-axial accelerometer. This improves the quality of the signal, i.e. of the motion signal, and facilitates therefore further processing of the signal. For example, an algorithm for automatically determining the breathing rate or the heart rate from the motion signal yields improved results, if the quality of the motion signal, on which the determination is based, is improved, in particular, if the signal-to-noise ratio of the motion signal is increased.

The multi-axial accelerometer is preferentially a tri-axial accelerometer being adapted to generate three accelerometer signals indicative of the acceleration along three orthogonal spatial axes, wherein the motion signal generation unit is adapted to combine these three accelerometer signals for generating the motion signal indicative of the motion of the object.

It is preferred that the multi-axial accelerometer is adapted to be positioned at a body part of a person, wherein the motion signal generation unit is adapted to generate a motion signal indicative of at least one of respiration and heart activity of the person. For generating a motion signal indicative of respiration the multi-axial accelerometer is preferentially positioned at the lower ribs, roughly half way between the central and lateral position. However, the multi-axial accelerometer can also be located at other positions, for example, on the abdomen, in particular, if limitations due to body physique like post-surgery wounds apply.

For generating a motion signal indicative of heart rate the multi-axial accelerometer is preferentially positioned on the left side of the abdomen/thorax. It is further preferred that the accelerometer is positioned at the lower-ribs, in particular, at the left lower ribs. A further preferred position of the multi-axial accelerometer for generating a motion signal indicative of heart rate is a higher position on the thorax or a lower position on the abdomen. In particular, the preferred positions for determining a motion signal indicative of respiration are also preferred for measuring a motion signal indicative of heart rate. Especially, for generating a motion signal indicative of respiration and heart rate the multi-axial accelerometer is preferentially positioned at the lower ribs, half way central-lateral on the left side.

It is preferred that the motion determination apparatus further comprises at least one of a breathing rate determination unit for determining a breathing rate and a heart rate determination unit for determining a heart rate depending on the generated motion signal.

This allows comfortable, low cost, continuous and ambulatory monitoring of the breathing rate and/or the heart rate.

In an embodiment, the fundamental frequency of the generated motion signal is the heart rate, if the accelerometer signals have been generated in a breath hold condition. If the accelerometer signals are generated while the person is breathing, the fundamental frequency of the motion signal is considered as corresponding to the breathing rate.

It is preferred that the motion determination apparatus further comprises a filtering unit for filtering the accelerometer signals such that frequencies corresponding to possible frequencies of the motion to be determined pass the filtering unit.

This reduces noise and possible further unwanted environmental influences on the accelerometer signals. If the motion signal should be indicative of respiration, the filtering unit is preferentially adapted to filter the accelerometers signals such that frequencies corresponding to possible frequencies of the respiration motion pass the filtering unit. In this case, frequencies within a frequency range of 0.1 to 2 Hz preferentially pass the filtering unit. If the motion signal generation unit is adapted to generate a motion signal indicative of the heart activity of the person, the filtering unit is preferentially adapted to filter the accelerometer signals such that frequencies corresponding to possible frequencies of heart activity motion pass the filtering unit, for example, the filtering unit can be adapted to filter the accelerometer signals such that frequencies within the frequency range of 0.5 Hz to 3 Hz pass the filtering unit.

It is further preferred that the motion signal generation unit is adapted to repeatedly generate the motion signal based on accelerometer signals generated in a temporally preceding time frame.

This allows to adapt the combination of the accelerometer signals to the actual conditions, for example, to the actual axial orientation of the multi-axial accelerometer. This allows, for example, determining the motion signal indicative of at least one of respiration and heart activity of a person, even if the person changes his/her posture. The time frame is, for example, a time frame of 20 seconds or smaller.

It is further preferred that the motion signal generation unit is adapted to combine the accelerometer signals such that the accelerometer signal having the largest acceleration change contributes mostly to the motion signal.

Since the accelerometer signal having the largest acceleration change is considered as having the largest signal-to-noise ratio, by combining the accelerometer signals such that the accelerometer signal having the largest acceleration change contributes mostly to the motion signal, the signal-to-noise ratio of the motion signal can be increased. Preferentially, the motion signal generation unit is adapted to combine the accelerometer signals such that the accelerometer signal having the largest acceleration change in a frequency range corresponding to the motion to be determined contributes mostly to the motion signal.

It is further preferred that the motion signal generation unit is adapted to linearly combine the accelerometer signals of different spatial axes, wherein the accelerometer signals are weighted such that the accelerometer signal having the largest acceleration change has the largest weight.

The motion signal generation unit is preferentially adapted to determine the weight of an accelerometer signal depending on a correlation of the respective accelerometer signal with the accelerometer signal having the largest acceleration change, wherein the weight of the respective accelerometer signal is larger if the respective correlation is larger.

This allows generating the motion signal such that the accelerometer signal having the largest acceleration change contributes mostly to the motion signal. Preferentially, the so-called "sample correlation coefficient" or "Pearson product-moment correlation coefficient" is used for determining the correlation.

It is further preferred that the motion signal generation unit is adapted to determine the weight of an accelerometer signal depending on a correlation of the respective accelerometer signal with the accelerometer signal having the largest acceleration change, wherein the weight of the respective accelerometer signal is the sign of the correlation.

This allows combining the accelerometer signals of the different spatial axes depending on their phase relationship such that the accelerometer signal having the largest acceleration change contributes mostly to the generated motion signal.

It is further preferred that the motion signal generation unit is adapted to apply a principal component analysis on the accelerometer signals of the different spatial axes and to determine a motion component from principal components resulting from the application of the principal component analysis, which is indicative of the motion to be determined, as the motion signal. Thus, a component of the principal components is selected as the motion component, i.e. as the motion signal. Preferentially, the motion signal generation unit is adapted to determine the first principal component as the generated motion signal.

Also the application of the principle component analysis and the use of a resulting component, in particular, of the resulting first principle component, as the generated motion signal allows combining the accelerometer signals such that the accelerometer signal having the largest acceleration change contributes mostly to the generated motion signal.

The principle component analysis is preferentially a standard orthogonal linear transformation that transforms the acceleration signals to a new coordinate system such that the greatest variance by any projection of the data comes to lie on the first principle component, the second greatest variance on the second principle component, and the third greatest variance on the third principle component.

It is further preferred that the motion signal generation unit is adapted to determine for each spatial axis of the accelerometer a maximized projection signal of the acceleration change and to generate the motion signal by combining the maximized projection signals, wherein the motion signal generation unit is adapted to determine the maximized projection signal of a spatial axis of the accelerometer by projecting a movement of a gravity vector relative to the spatial axes of the accelerometer on a subspace defined by the gravity vector and the respective spatial axis of the accelerometer and by transforming the respective axis within the subspace such that a projection of the projected movement of the gravity vector, which has been projected into the subspace, on the transformed respective axis is maximized. The subspace is preferentially a plane. The nominal gravity vector is a vector oriented such that it indicates the average of the movement of the gravity vector with respect to the different spatial axes of the accelerometer, i.e. the movement of the gravity vector can be described as variations with respect to the nominal gravity vector.

It is further preferred that the motion signal generation unit is adapted to generate the motion signal by determining a vector magnitude of the maximized projection signals and by combining the determined vector magnitude with the sign of at least one of the maximized projection signals. Preferentially, the determined vector magnitude is multiplied by the sign of at least one of the maximized projection signals. It is further preferred that the determined vector magnitude is multiplied by the sign of the maximized projection signal having the largest amplitude.

This allows generating a motion signal having an increased signal-to-noise ratio.

It is further preferred that the motion signal generation unit is adapted to apply a principal component analysis on the maximized projection signals, wherein the resulting first principal component is the generated motion signal.

This also allows combining the accelerometer signals of the different spatial axes such that the accelerometer signal having the largest acceleration change contributes mostly to the motion signal.

It is further preferred that the motion signal generation unit is adapted to apply an independent component analysis on the accelerometer signals of the different spatial axes and to determine a motion component from the independent components resulting from the application of the independent component analysis, which is indicative of the motion to be determined as the motion signal. Thus, a component of the independent components is selected as the motion component, i.e. as the motion signal.

Also this allows generating the motion signal such that the accelerometer signal having the largest acceleration changes contributes mostly to the motion signal.

Preferentially, an algorithm that exploits the temporal correlation in the signals, such as the so-called SOBI algorithm, is used for applying the independent component analysis on the accelerometer signals. The SOBI algorithm is disclosed in the article "A blind source separation technique using second order statistics," Belouchrani A. et al., IEEE Trans Signal Process, 45(2): 434-444, February 1997, which is herewith incorporated by reference.

The motion component from the independent components resulting from the application of the independent component analysis, which is indicative of the motion to be determined, can be determined by determining the independent component having the largest amplitude at a predetermined frequency. For example, if a respiration rate or heart rate should be determined based on the motion signal, the independent component having the largest amplitude within a frequency interval, which corresponds to possible breathing rates or heart rates, is determined as the motion component.

The motion determination apparatus comprises preferentially several multi-axial accelerometers for being positioned at the object at complementary positions, wherein the motion signal generation unit is adapted to generate a motion signal indicative of the motion of the object by combining the accelerometer signals of different spatial axes of the several multi-axial accelerometers.

This allows further increasing the signal-to-noise ratio and further reducing the probability of not determining the motion of the object. Two positions on the object are preferentially regarded as being complementary, if the motion at these two positions is different, in particular, if the motion-induced changes with respect to gravity at the two positions are different. In particular, two positions on the object are regarded as being complementary, if the motion induced by respiration or by heart activity is different at these positions, especially if the respiration-induced changes or the heart activity induced changes with respect to gravity are different at these positions.

If the motion determination apparatus comprises several multi-axial accelerometers, the motion signal generation unit is preferentially adapted to generate a motion signal by combining the accelerometer signals of the different spatial axes of the several multi-axial accelerometers by using a principle component analysis or an independent component analysis.

Preferentially, two multi-axial accelerometers are positioned at the object, in particular, two tri-axial accelerometers are preferentially positioned at the object. The first accelerometer is preferentially positioned as described above at, for example, the lower ribs and the second accelerometer is preferentially positioned centrally at the upper thorax, for example, at the sternum.

In a further aspect of the present invention a motion determination method for determining motion of a moving object is presented, wherein the motion determination method comprises following steps:

generating accelerometer signals indicative of the acceleration along different spatial axes by a multi-axial accelerometer being positioned at the moving object, generating a motion signal indicative of the motion of the object by combining the accelerometer signals of different spatial axes by a motion signal generation unit. In a further aspect of the present invention a computer program for determining motion of a moving object is presented, wherein the computer program comprises program code means for causing a motion determination apparatus to carry out the steps of the motion determination method, when the computer program is run on a computer controlling the motion determination apparatus.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF EMBODIMENTS

Figure 1:
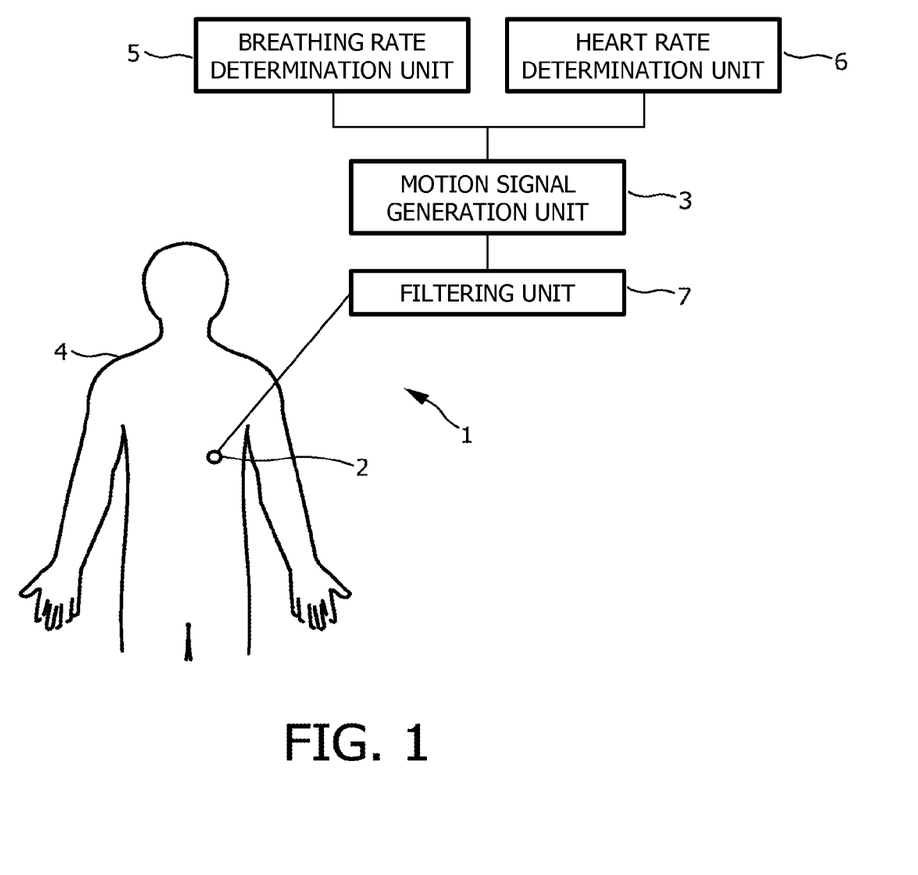
FIG. 1 shows schematically and exemplarily an embodiment of a motion determination apparatus.

FIG. 1 shows schematically and exemplarily a motion determination apparatus for determining motion of a moving object. The motion determination apparatus 1 comprises a multi-axial accelerometer 2 for being positioned at the moving object 4. The multi-axial accelerometer 2 is adapted to generate accelerometer signals indicative of the acceleration along different spatial axes. In this embodiment, the multi-axial accelerometer is a tri-axial accelerometer being adapted to generate three accelerometer signals indicative of the acceleration along three orthogonal spatial axes. For example, tri-axial accelerometers named ST Microelectronics LIS344ALH or Kionix KXM52 can be used. However, also other kinds of multi-axial accelerometers can be used for generating accelerometer signals indicative of the acceleration along different spatial axes.

The motion determination apparatus 1 further comprises a motion signal generation unit 3 for generating a motion signal indicative of the motion of the object 4 by combining the accelerometer signals of different spatial axes. In this embodiment, the motion signal generation unit 3 is adapted to combine the three accelerometer signals of the tri-axial accelerometer 2 for generating the motion signal indicative of the motion of the object 4.

The object 4 is, in this embodiment, a body 4 of a person, wherein the multi-axial accelerometer 2 is positioned at the body 4 of the person and wherein the motion signal generation unit 3 is adapted to generate a motion signal indicative of at least one of respiration and heart activity of the person.

The multi-axial accelerometer 2 is positioned at the left lower ribs, roughly half way between the central and lateral position. However, the multi-axial accelerometer 2 can also be located at other positions, for example, on the abdomen, in particular, if limitations due to body physique like post-surgery wounds apply.

The motion determination apparatus 1 further comprises a filtering unit 7 for filtering the accelerometer signals such that frequencies corresponding to possible frequencies of the motion to be determined pass the filtering unit 7. This reduces noise and possible further unwanted environmental influences on the accelerometer signals. In this embodiment, the motion signal should be indicative of respiration or heart rate. The filtering unit 7 is therefore adapted to filter the accelerometer signals such that frequencies corresponding to possible frequencies of respiration motion or motion caused by heart activity pass the filtering unit. In particular, the filtering unit 7 can be adapted to filter frequencies within a frequency range of 0.1 to 3 Hz. It is also possible that for determining respiration frequencies within a frequency range of 0.1 to 2 Hz are filtered and that for determining heart rate frequencies within a frequency range of 0.5 to 3 Hz are filtered, i.e. pass the filtering unit 7.

The motion determination apparatus further comprises a breathing rate determination unit 5 for determining a breathing rate depending on the generated motion signal and a heart rate determination unit 6 for determining a heart rate depending on the generated motion signal. If the filtering unit 7 is adapted to filter the accelerometer signals with a first filter for filtering the accelerometer signals for determining respiration and if the filtering unit 7 is adapted to filter the accelerometer signals with a second filter for filtering the accelerometer signals for determining heart rate, the accelerometer signals filtered with the first filter are preferentially combined separately from the accelerometer signals filtered with the second filter, wherein the motion signal generated by combining the accelerometer signals filtered by the first filter are provided to the breathing rate determination unit 5 and the motion signal generated by combining the accelerometer signals filtered by the second filter is provided to the heart rate determination unit 6.

The breathing rate is preferentially determined by the breathing rate determination unit 5 as the fundamental frequency of the motion signal provided to the breathing rate determination unit 5. The heart rate is preferentially determined by determining the fundamental frequency of the motion signal provided to the heart rate determination unit 6.

In a further preferred embodiment, the breathing rate is determined by the breathing rate determination unit 5 as the reciprocal of the time interval between consecutive peaks in the motion signal. The peaks in the motion signal can be determined by identifying the zero-crossings of the first derivative of the motion signal. In order to avoid the detection of false peaks, additional restrictions can be imposed on the peaks. For example, only those peaks of the motion signal that exceed a threshold are used for the breathing rate determination. The threshold can, for example, be determined by calibration.

The motion signal generation unit 3 is adapted to repeatedly generate the motion signal based on accelerometer signals generated in a temporarily preceding time frame. This allows to adapt the combination of the accelerometer signals to the actual conditions, for example, to the actual orientation of the multi-axial accelerometer. This allows, for example, determining a motion signal indicative of at least one of respiration and heart activity of a person, even if the person changes his/her posture. The time frame is preferentially 20 seconds or smaller, further preferred 10 seconds or smaller and even further preferred 5 seconds or smaller.

The motion signal generation unit 3 is adapted to combine the accelerometer signals such that the accelerometer signal having the largest acceleration change contributes mostly to the motion signal. In this embodiment, the motion signal generation unit 3 is adapted to apply a principle component analysis on the accelerometer signals of the different spatial axes, wherein the resulting first principle component is the generated motion signal.

The effect of combining the three accelerometer signals, in particular, by performing a principle component analysis, for generating a motion signal will in the following be described with reference to FIGS. 2 and 3.

Figure 2:
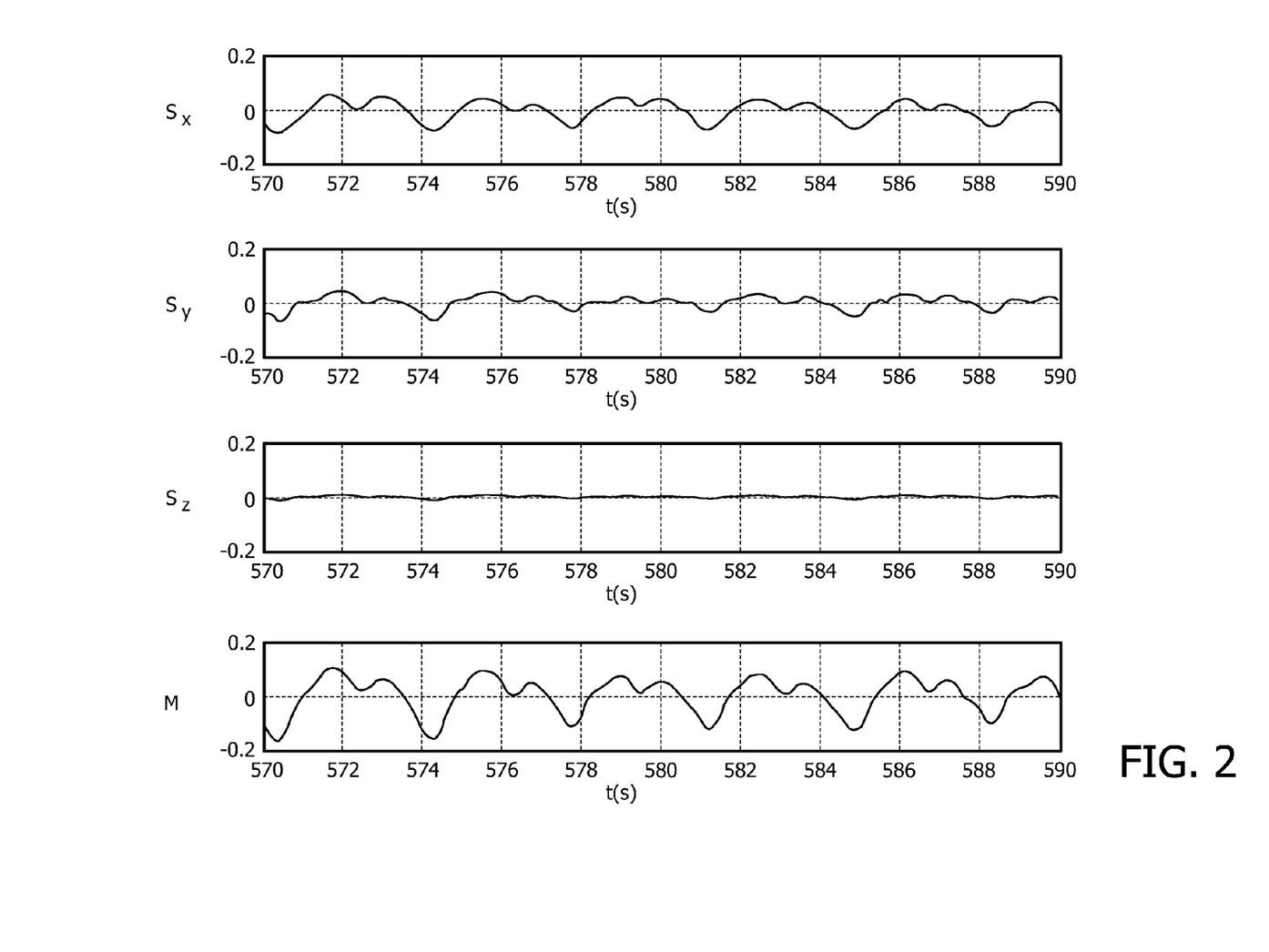
FIG. 2 shows exemplarily three accelerometer signals and a motion signal generated by combining the accelerometer signals before a posture change of an object.

FIG. 2 shows schematically and exemplarily accelerometer signals $S_x, S_y, S_z$ in arbitrary units depending on the time t in seconds. Because of the orientation of the tri-axial accelerometer with respect to the motion to be determined the accelerometer signal $S_x$ shows the largest variations caused by motions of the person at the position at which the tri-axial accelerometer 2 is located, whereas the accelerometer signal $S_z$ shows only small variations. The combination of these accelerometer signals $S_x, S_y, S_z$ yields a motion signal M showing relatively large variations and having therefore a relatively large signal-to-noise ratio.

Figure 3:
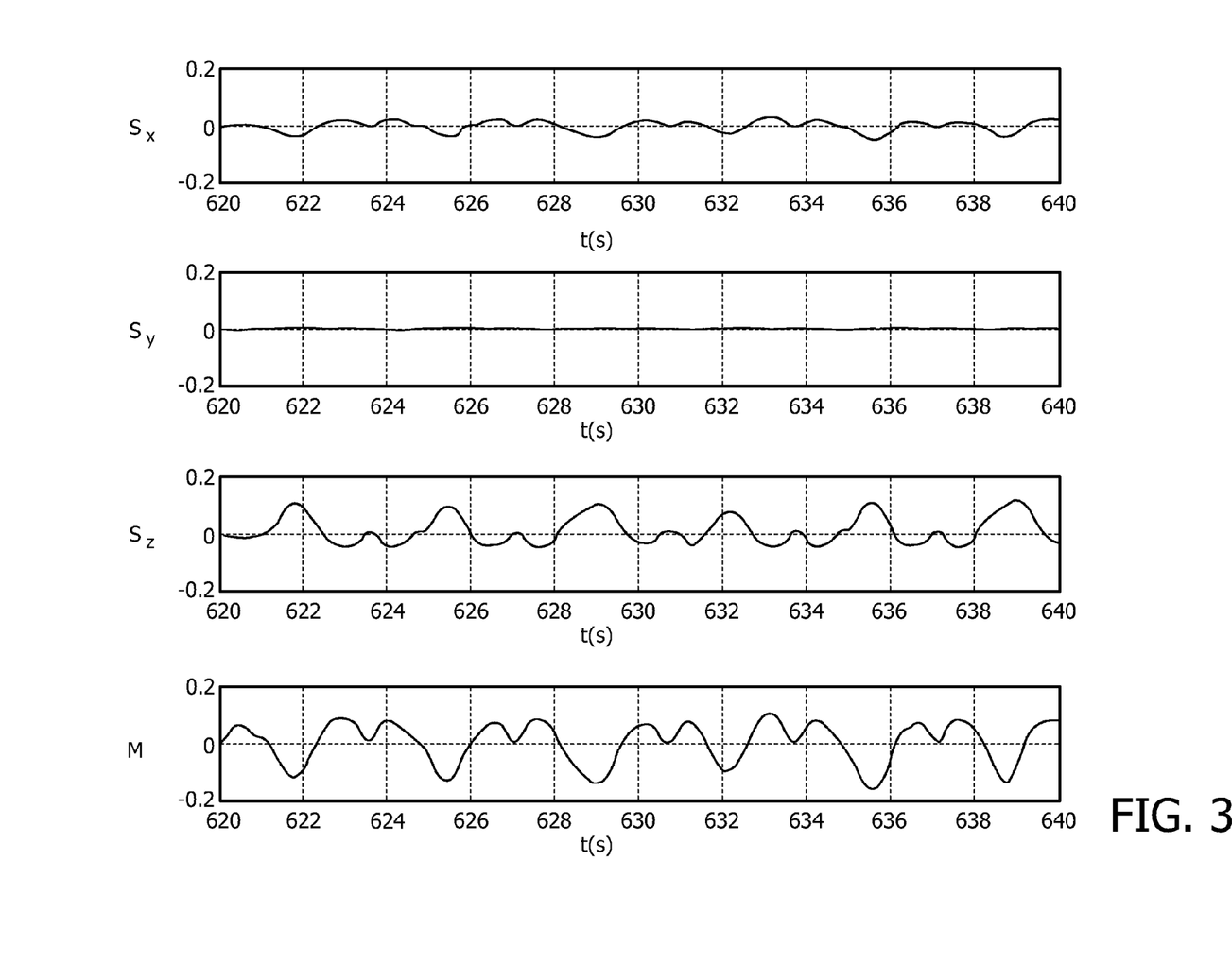
FIG. 3 shows exemplarily the three accelerometer signals and a motion signal generated by combining the three accelerometer signals after the posture change of the object.

FIG. 3 shows the same accelerometer signals after the posture of the person 4 has been changed. After this posture change the accelerometer signal $S_z$ shows the largest variations, whereas the accelerometer signal $S_y$ shows the smallest variations. However, because of the combination of the three accelerometer signals performed by the motion signal generation unit 3, a motion signal M is generated, which still shows relatively large variations and which has therefore still a relatively large signal-to-noise ratio. Thus, even after the posture of the person has been changed, the generated motion signal still shows large variations and has a large signal-to-noise ratio. In FIGS. 2 and 3 the variations or fluctuations in the signal with a period of about four seconds are caused by respiration. Thus, a breathing rate of 15 breaths per minute can be determined from the motion signal shown in FIGS. 2 and 3.

In a further preferred embodiment, the motion signal generation unit is adapted to linearly combine the accelerometer signals of different spatial axes, wherein the accelerometer signals are weighted such that the accelerometer signal having the largest acceleration change, has the largest weight. For example, the motion signal generation unit can be adapted to determine the weight of an accelerometer signal depending on a correlation of the respective accelerometer signal with the accelerometer signal having the largest acceleration change, wherein the weight of the respective accelerometer signal is larger if the respective correlation is larger.

The correlation is preferentially determined by determining the "sample correlation coefficient" or "Pearson product-moment correlation coefficient".

The generation of the motion signal M by linearly combining the accelerometer signals $S_x, S_y, S_z$ can be described by following equation:

$$M = w_x S_x + w_y S_y + w_z S_z, \quad (1)$$

wherein $w_x, w_y, w_z$ represent the respective weights.

The weighting factors $w_x, w_y, w_z$ are preferentially determined such that the motion signal has the largest signal-to-noise ratio. These weighting factors depend on the orientation of the accelerometer, in particular, on the posture of the person to which the multi-axes accelerometer is attached, therefore the weighting factors $w_x, w_y, w_z$ are preferentially updated regularly. The weighting factors are calculated at regular time instances, for example, every second, based on the accelerometer signals of a certain preceding time frame, which is preferentially 20 seconds or smaller. Preferentially, the motion signal generation unit is adapted to linearly interpolate between weighting factors, which have been determined at a first time instance, and weighting factors, which have been determined at second time instance, if the weighting factors have been changed between these two time instances, in order to assure a smooth motion signal waveform.

In a preferred embodiment, the weighting factors are +1 or −1 according to the phase relationship between the accelerometer signals. The sign is preferentially determined based on the correlation coefficient between a reference axis and the two other axes, for example, if the x-axis is the reference axis, the weighting factors are preferentially defined by following equations:

$$w_x = 1, \quad (2)$$

$$w_y = \text{sign}(C(S_x, S_y)), \quad (3)$$

$$w_z = \text{sign}(C(S_x, S_z)), \quad (4)$$

wherein sign ( . . . ) is a sign function and wherein C ( . . . ) represents the correlation coefficient between the respective accelerometer signals. Preferentially, the accelerometer axis having the accelerometer signal with the largest amplitude in a frequency range, which corresponds to possible frequencies of the motion to be determined, is considered as reference axis.

Also the first principle component determined by applying a principle component analysis to the three accelerometer signals can be regarded as a linear combination of the three accelerometer signals, because the principle component analysis is an orthogonal linear transformation, in particular, a rotation, that decomposes the three accelerometer signals in a linear mixture of uncorrelated components, the so-called principle components. The principle components are obtained by an eigenvalue decomposition of the co-variance matrix of the three accelerometer signals. The first principle component is the linear combination of the three accelerometer signals that accounts for the largest variance in the accelerometer signals. If, for example, respiration is the largest source of variance in the accelerometer signals, the application of the principle component analysis on the three accelerometer signals generates a first principle component being a combination of the three accelerometer signals which maximizes the motion signal induced by respiration. In order to ensure that respiration is the largest source of variance in the accelerometer signals, the accelerometer signals can be filtered by the filtering unit 7 such that the accelerometer signals are restricted to a frequency band corresponding to a respiration rate that is physiologically possible, for example, to a frequency band of 0.1 to 2 Hz, which corresponds to 6 to 120 breaths per minute.

In a further embodiment, the motion signal generation unit 3 is adapted to apply an independent component analysis on the accelerometer signals of the different spatial axes and to determine a motion component from the independent components resulting from the application of the independent component analysis, which is indicative of the motion to be determined, as the motion signal.

The independent component analysis can be regarded as an extension of the principle component analysis that finds linear combinations of the accelerometer signals that are not only uncorrelated but statistically independent. To this end, independent component analysis algorithms exploit additional information not contained in the co-variance matrix, usually higher-order statistics. Since the motion signal to be determined, in particular, the motion signal caused by respiration and/or heart activity, is temporarily correlated, the SOBI algorithm is preferentially used for performing the independent component analysis because the SOBI algorithm exploits the time structure of the accelerometer signals. The SOBI algorithm is based on a simultaneous diagonalization of a set of co-variance matrices at different time lags. Contrary to the principle component analysis, the independent components obtained with the independent component analysis are not ranked according to variance. Thus, even if respiration and/or heart activity accounts for the largest variance in the accelerometer signals, the independent component related to respiration and/or heart rate is not necessarily the first one. The motion signal generation unit is therefore adapted to determine the independent component, which is indicative of the motion to be determined, as the motion signal.

The motion signal generation unit can be adapted to determine the motion component from the independent components resulting from the application of the independent component analysis, which is indicative of the motion to be determined, by determining the independent component having the largest amplitude at a predetermined frequency, which is indicative of the motion to be determined. For example, if a respiration rate or a heart rate should be determined based on the motion signal, the independent component whose power spectrum has the largest peak within a frequency interval, which corresponds to possible breathing rates or possible heart rates, respectively, is determined as the motion component.

In a further embodiment, the independent component that is indicative of the motion can be determined based on a score that takes into account additional features. The independent component with the smallest score is then selected as the one that is indicative of the motion. For example, the score could be calculated as the sum of a number of features of the independent components:

$$\text{Score}(IC_x) = \sum_{i=1}^{N} w_i \cdot F_i(IC_x), \quad (5)$$

where $\text{Score}(IC_x)$ represents the score of the x-th independent component, N the number of features that is used, $F_i(IC_x)$ the value of the i-th feature for the x-th independent component, and $w_i$ the weight corresponding to the i-th feature. Preferred features are, for example, based on the fundamental frequency of the independent component, the mixing weights of the independent component, the spectral shape of the independent component, et cetera. As changes in breathing, heart rate and posture usually take place gradually over time, also features that take into account knowledge about the breathing, heart rate and/or posture in a previous time interval can be used. For example, the absolute difference of the fundamental frequency of an independent component and the fundamental frequency of the motion signal in a previous time interval could be used as a feature. For the first time interval that is analyzed, the selection of the independent component that is indicative of the motion can be based on (1) only those features that do not rely on knowledge from previous time intervals, or (2) on estimating initial values for the features of the previous data.

In an embodiment, the above described methods for determining an independent component, which is indicative of the motion to be determined, as the motion signal, can also be applied to determine a principal component resulting from a principal component analysis, which is indicative of the motion to be determined, as the motion signal.

In a further embodiment, the motion signal generation unit 3 is adapted to determine for each spatial axis of the accelerometer a maximized projection signal of the acceleration change and to generate the motion signal by combining the maximized projection signals, wherein the motion signal generation unit is adapted to determine the maximized projection signal of a spatial axis of the accelerometer by projecting a movement of a gravity vector relative to the spatial axes of the accelerometer on a subspace defined by the nominal gravity vector and the respective spatial axis of the accelerometer and by transforming the respective axis within the subspace such that a projection of the projected movement of the gravity vector, which has been projected into the subspace, on the transformed respective axis is maximized.

Since the inertial acceleration due to the movement, for example, due to respiration or heart activity, is much smaller than the gravitational acceleration, the axes, in particular, the three orthogonal axes of the accelerometer, represent the projections of the gravity vector on each axis x,y,z. This is exemplarily illustrated in FIG. 4.

Figure 4:
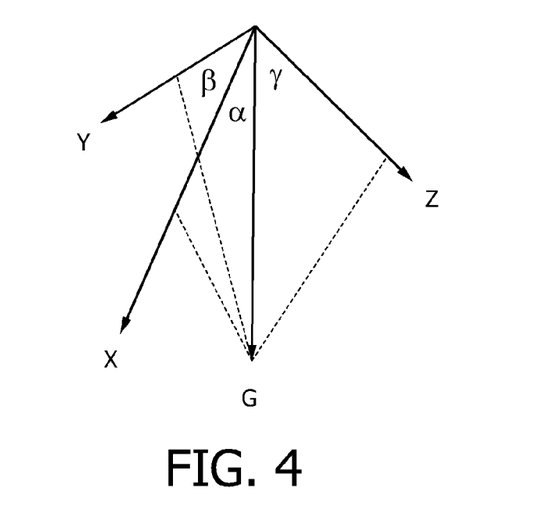
FIG. 4 illustrates a spatial relationship between a gravity vector and different spatial axes of the accelerometer.

The value on each axis x,y,z of the accelerometer is the projection of the gravity vector on the respective axis. This value is determined by the angles between the gravity vector and the respective axis, i.e. by the angles $\alpha,\beta,\gamma$, respectively, and following equations:

$$S_x = G \cdot \cos \alpha, \quad (6)$$

$$S_y = G \cdot \cos \beta, \quad (7)$$

$$S_z = G \cdot \cos \gamma, \quad (8)$$

wherein G represents the absolute value of the gravity vector.

Figure 5:
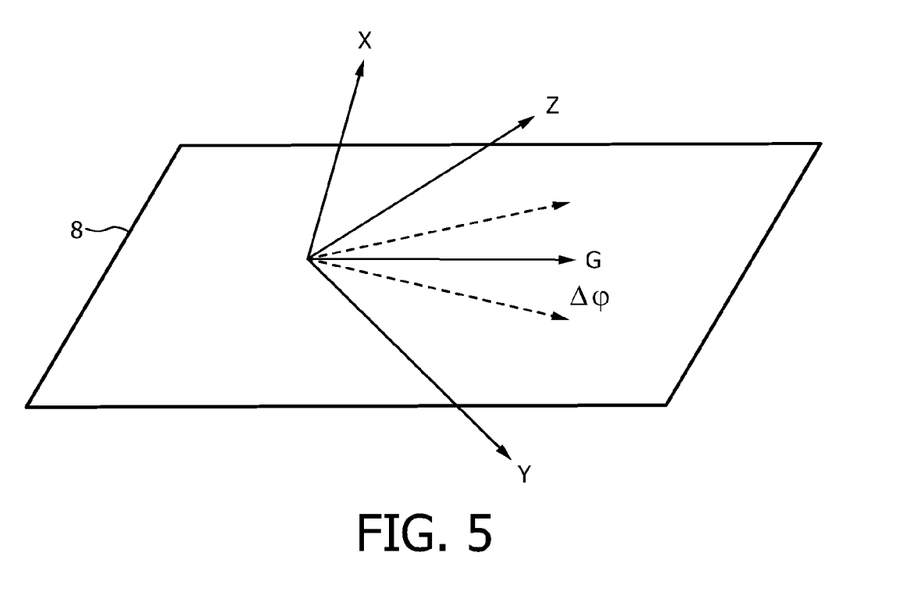
FIG. 5 illustrates a movement of the gravity vector with respect to the different spatial axes of the accelerometer.

If it is assumed that the accelerometer motion due to, for example, respiration or heart activity, takes place in a plane, this movement can be represented in the sensor coordinate system as the gravity vector G moving back and forth around a nominal location in an arbitrary plane 8. This is exemplarily illustrated in FIG. 5. In FIG. 5 $\Delta\phi$ denotes the full angle span on each side of the nominal location of the gravity vector G.

Figure 6:
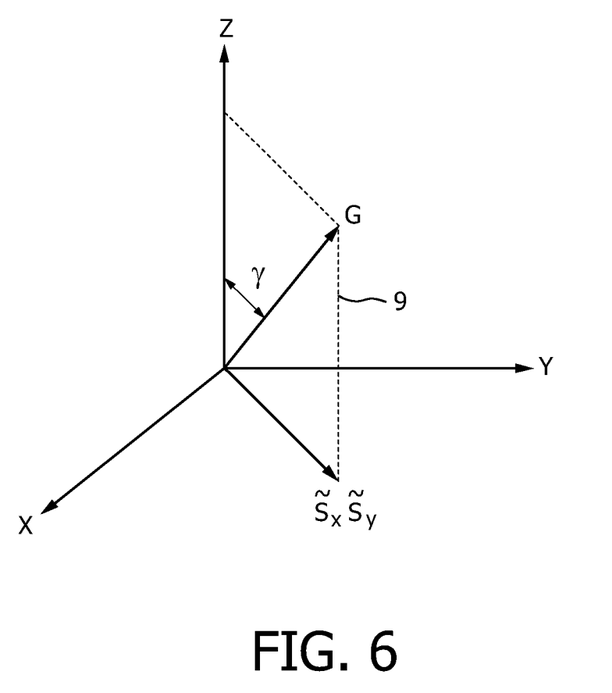
FIG. 6 shows a subspace of one of the different spatial axes of the accelerometer.

For each spatial axis x, y, z a subspace, i.e. a two-dimensional plane, is defined by the gravity vector G and the respective spatial axis x, y, z. Such a subspace 9 is schematically and exemplarily shown in FIG. 6 for the z-axis. In FIG. 6 $\gamma$ denotes the angle between the gravity vector at the nominal location and the respective spatial axis of the accelerometer, and $\tilde{S}_x \tilde{S}_y$ is the vector sum of the x-coordinate and y-coordinate of the gravity vector, i.e. the vector sum of $S_x$ and $S_y$.

For each such spatial axis, the movement of the gravity vector is first projected onto the corresponding subspace, defined by the respective spatial axis and the nominal location of the gravity vector. Subsequently, in this subspace, the z-axis is rotated such that the amplitude change—due movement of the gravity vector—in this new Z-axis is maximized.

In its nominal location, the projection of the gravity vector on the rotated axis can be written as:

$$P_{max,z}(0) = -S_Z \cdot \sin\gamma + \tilde{S}_x \tilde{S}_y \cdot \cos\gamma \quad (9)$$
$$= -S_Z \cdot \sin\gamma + \sqrt{S_x^2 + S_y^2} \cdot \cos\gamma$$
$$= -G \cdot \cos\gamma \cdot \sin\gamma + G \cdot \sin\gamma \cdot \cos\gamma.$$

In its most extreme position, the projection of the gravity vector on the rotated axis can be written as:

$$P_{max,z}(\Delta\gamma) = -G \cdot \cos(\gamma+\Delta\gamma) \cdot \sin\gamma + G \cdot \sin(\gamma+\Delta\gamma) \cdot \cos\gamma, \quad (10)$$

wherein $\Delta\gamma$ denotes the angle span on each side of the nominal location of the gravity vector in the respective subspace and $\gamma$ denotes the nominal value of $\gamma$.

Combining equations (9) and (10) using trigonometric sum formulas shows that the resulting amplitude of the rotated projection of the gravity vector is related to the angle span $\Delta\gamma$:

$$\Delta P_{max,z} = G \cdot \sin(\Delta\gamma). \quad (11)$$

The term "$\sin(\Delta\gamma)$" is the maximized projection of the acceleration change, i.e. of the movement, which is preferentially caused by respiration or heart activity, in the subspace. In order to determine the maximized projection signal, i.e. in order to determine $G \cdot \sin(\Delta\gamma)$, by using equation (9), $\sin\gamma$ or $\cos\gamma$ have to be determined. The value $\cos\gamma$ and, thus, also the value $\sin\gamma$ can be determined in accordance with following equation:

$$\cos\gamma = \frac{\text{mean}(S_z)}{1 - \frac{(\Delta\gamma)^2}{6}} \quad (12)$$
$$= \frac{\text{mean}(S_z)}{1 - \frac{(\arccos(\text{mean}(\max(S_z)) = \text{mean}(\min(S_z)))/2)^2}{6}},$$

wherein $\text{mean}(S_z)$ is the average of the accelerometer signal of the z-axis over a time interval of, for example, 20 seconds or smaller, wherein $\text{mean}(\max(S_z))$ is the average of the peak amplitude of the accelerometer signal $S_z$ of the z-axis and wherein $\text{mean}(\min(S_z))$ is the average of the valley amplitude of the accelerometer signal $S_z$ of the z-axis. Equation (12) is derived using Tailor expansion of the projection of an ideal movement signal.

The above described determination of a maximized projection signal for the z-axis is correspondingly performed for the other axes, i.e. for the x-axis and the y-axis, such that for each spatial axis of the accelerometer a maximized projection signal is determined. In this embodiment, the motion signal generation unit is adapted to combine the maximized projection signals $P_{max,x}, P_{max,y}, P_{max,z}$ of the three spatial axis x, y, z for generating a motion signal. The motion signal generation unit can be adapted to perform this combining by using the principle component analysis, wherein the first principle component is the generated motion signal. The motion signal generation unit can also be adapted to determine the vector magnitude of the three maximized projection signals for generating a motion signal. This determination of the vector magnitude is preferentially performed in accordance with following equation:

$$M = \sqrt{P_{max,x}^2 + P_{max,y}^2 + P_{max,z}^2} \cdot \text{sign}(P_{max,i\,max}), \quad (13)$$

wherein $\text{sign}(\ldots)$ represents the sign function and $P_{max,i\,max}$ that maximized projection which has the largest motion signal amplitude, i.e. wherein the index i max denotes the maximized projection having the largest signal amplitude, i.e. x, y or z.

Figure 7:
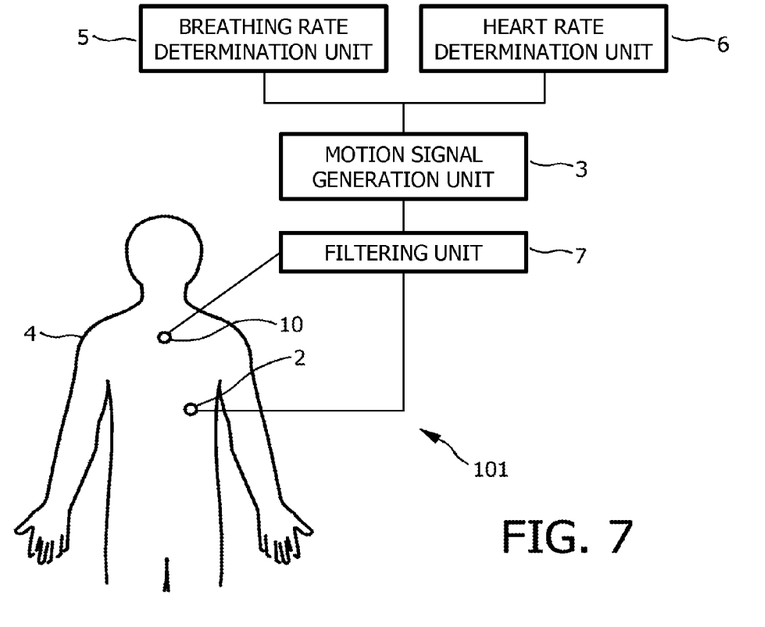
FIG. 7 shows a further embodiment of the motion determination apparatus.

FIG. 7 shows a further embodiment of the motion determination apparatus comprising several multi-axial accelerometers 2, 10, in particular, two three-axial accelerometers, for being positioned at the person 4 at complementary positions, wherein the filtering unit 7 is adapted to filter the accelerometer signals of these multi-axial accelerometers 2, 10 and wherein the motion signal generation unit is adapted to generate a motion signal indicative of the motion of the person 4, in particular, indicative of motion caused by respiration and/or heart activity of the person 4, by combining the accelerometer signals of the different spatial axes of the several multi-axial accelerometers 2, 10. In this embodiment, the motion signal generation unit is preferentially adapted to generate a motion signal by combining the accelerometer signals of the different spatial axes of the several-multi accelerometers 2, 10 by using the above described principle component analysis or the above described independent component analysis. In particular, each tri-axial accelerometer 2, 10 generates three orthogonal accelerometer signals, i.e. six accelerometer signals are generated, wherein a principle component analysis or an independent component analysis is applied to these six accelerometer signals.

The first accelerometer 2 is positioned at the left lower ribs and the second accelerometer 10 is located centrally at the upper thorax, for example, at the sternum.

Figure 8:
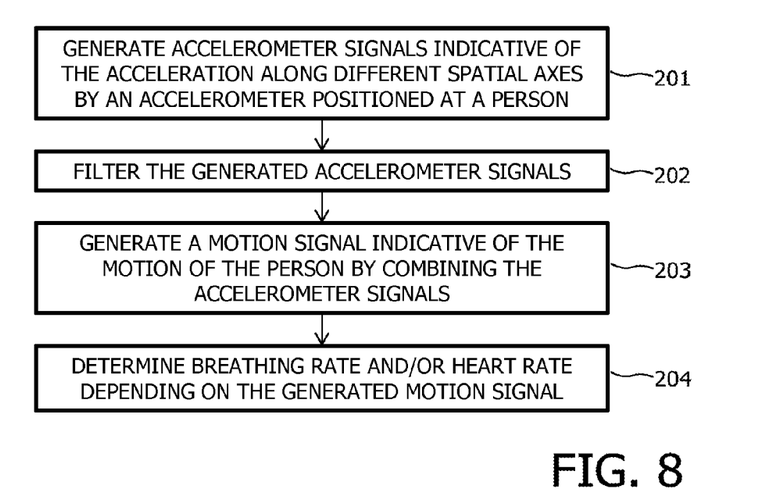
FIG. 8 shows a flowchart exemplarily illustrating an embodiment of a motion determination method.

In the following a motion determination method for determining motion of a moving object will be exemplarily described with reference to a flowchart shown in FIG. 8.

In step 201, accelerometer signals indicative of the acceleration along different spatial axes are generated by a multi-axial accelerometer being positioned at the person 4. In step 202, the filtering unit 7 filters the generated accelerometer signals, and in step 203, the motion signal generation unit generates a motion signal indicative of the motion of the person 4 by combining the accelerometer signals of the different spatial axes, in particular, a motion signal is generated indicative of motion caused by respiration and/or heart activity.

In step 204, the breathing rate is determined by the breathing rate determination unit 5 and/or the heart rate is determined by the heart rate determination unit 6 depending on the generated motion signal.

The motion determination apparatus comprises one or more multi-axial accelerometers, which are preferentially positioned at the chest and/or abdomen of a person, in order to monitor respiration and/or heart rate, in particular, under ambulatory conditions. In contrast to known accelerometer-based respiration monitoring systems, which rely on the accelerometer data of single axis, the motion determination apparatus in accordance with the invention exploits the accelerometer signals of different spatial axes simultaneously. This is particularly helpful in ambulatory conditions, where the orientation of the accelerometer not only changes due to respiration or heart activity, but also due to a posture changes and patient movement.

The multi-axial accelerometer is used as an inclinometer to reflect the movement of the object, in particular, to reflect the movement of the abdomen or the chest caused by respiration and/or heart activity. The movement is reflected by an inclination change of a surface of the object, on which the multi-axial accelerometer is positioned. The several spatial axes of the multi-axial accelerometer, which are preferentially three orthogonal axes, record the accelerometer signals equal to the projection of the gravity vector on each of these axes. Since the components $S_x, S_y, S_z$ of the gravity vector are determined by the angles between the gravity vector and each respective axis, the change of inclination of the accelerometer caused by a movement of the object, can be reflected by the change of the accelerometer signals $S_x, S_y, S_z$, wherein it is assumed that a further external acceleration of the object, which could also contribute to the accelerometer signals $S_x, S_y, S_z$, is small compared with gravity. This assumption is valid at least in situations, in which a motion signal indicative of a motion caused by respiration and/or heart activity has to be generated in an ambulatory environment.

The motion determination apparatus can be used for patient monitoring, in particular, to aid in detecting the acutely ill patients outside the intensive care areas.

The motion determination apparatus combines the accelerometer signals of the different spatial axes in an optimal and automated manner such that a signal-to-noise ratio of a motion signal, which is preferentially used to determine a breathing rate and/or a heart rate, has an optimised signal-to-noise ratio. In particular, the motion determination apparatus allows to automatically track the optimal combination of the accelerometer signals of the different spatial axes, even if the posture of the object, for example, the posture of a person who is monitored, is changed. In particular, the amplitude of the generated motion signal is generally larger than the amplitude of each of the accelerometer signals of the different spatial axes of the accelerometer. The motion determination apparatus is preferentially used in a setting where respiration and/or heart rate is monitored in an ambulatory environment using one or more multi-axial accelerometers.

The noise in the different spatial axes is generally uncorrelated and the motion signal is generally correlated. By combining the accelerometer signals of the different spatial axes for generating the motion signal the signal-to-noise ratio can therefore be increased. In particular, the motion signal generation unit is preferentially adapted such that the ratio of the motion-related changes to the noise-related changes is at least as large as in the individual spatial axis that has the largest ratio of motion-related changes to noise-related changes, irrespective of the orientation of the object and the movement.

Although in the above described embodiments the multi-axial accelerometer has preferentially three orthogonal axes, the multi-axial accelerometer can also have two orthogonal axes or more than three axes. Furthermore, the spatial axis can also include another angle, i.e. in another embodiment the axes can be non-orthogonal.

Although in the above described embodiments, one or two multi-axial accelerometers are used, also more than two accelerometers can be used for determining motion of an object, in particular, for determining a motion signal indicative of the motion of the object and for determining a breathing rate and/or a heart rate depending on the determined motion signal.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of the motion signal, the breathing rate or the heart rate and the filtering of the accelerometer signals performed by one or several units or devices can be performed by any other number of units or devices. For example, the determination of the motion signal and the determination of the breathing rate and/or the heart rate depending on the motion signal can be performed by a single unit or by any other number of different units. The determinations and/or the filtering and/or the control of the motion determination apparatus in accordance with the motion determination method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A motion determination apparatus for determining respiration and heart activity, wherein the motion determination apparatus comprises:
    at least one accelerometer configured to be positioned on a subject, wherein the at least one accelerometer is adapted to generate accelerometer signals indicative of the acceleration along at least three different spatial axes; and
    at least one computer configured to generate motion signals indicative of respiration and heart activity including respiratory rate and heart rate by combining the accelerometer signals of different spatial axes;
    wherein the at least one computer is further configured to linearly combine the accelerometer signals of different spatial axes, wherein the accelerometer signals are weighted such that the accelerometer signal having the largest acceleration change has the largest weight;
    wherein the at least one computer is further configured to determine the weight of an accelerometer signal depending on a correlation of the respective accelerometer signal with the accelerometer signal having the largest acceleration change, wherein the weight of the respective accelerometer signal is the sign of the correlation;
    wherein the motion determination apparatus further comprises:
        a heart rate determination device configured to determine a heart rate depending on the weight of the respective accelerometer signal.

2. A motion determination apparatus for determining motion of a moving object, wherein the motion determination apparatus comprises:
    a multi-axial accelerometer for being positioned at the body of a person, wherein the multi-axial accelerometer is adapted to generate accelerometer signals indicative of the acceleration along different spatial axes;
    a motion signal generation device configured to generate a motion signal indicative of heart activity of the person by combining the accelerometer signals of different spatial axes, wherein the motion signal generation unit is adapted to determine for each spatial axis of the accelerometer a maximized projection signal of the acceleration change and to generate the motion signal by combining the maximized projection signals, wherein the motion signal generation unit is adapted to determine the maximized projection signal of a spatial axis of the accelerometer by projecting a movement of a gravity vector relative to the spatial axis of the accelerometer on a subspace defined by the nominal gravity vector and the respective spatial axis of the accelerometer and by transforming the respective axis within the subspace such that a projection of the projected movement of the gravity vector, which has been projected into the subspace, on the transformed respective axis is maximized; and
    a heart rate determination device configured to determine a heart rate depending on the generated motion signal.

3. The motion determination apparatus as defined in claim 2, wherein the motion signal generation unit is adapted to generate the motion signal by determining a vector magnitude of the maximized projection signals and by combining the determined vector magnitude with the sign of at least one of the maximized projection signals.

4. The motion determination apparatus as defined in claim 2, wherein the motion signal generation unit is adapted to apply a principal component analysis on the maximized projection signals, wherein the resulting first principal component is the generated motion signal.

5. A motion determination method for determining a heart rate of a subject, wherein the motion determination method comprises following steps:
    receiving accelerometer signals indicative of acceleration along different spatial axes from a multi-axial accelerometer positioned on the moving object; and
    generating a heart rate signal indicative of the heart rate of the subject by combining the accelerometer signals of different spatial axes, the generating of the heart rate signal including:
        determining for each spatial axis of the accelerometer a maximized projection signal of the acceleration change using the movement of a gravity vector relative to the spatial axis; and
        combining the maximized projection signals.

6. A non-transitory computer readable medium carrying program code for causing a processor to perform the method of claim 5.

7. A motion determination apparatus for determining motion of a moving object, wherein the motion determination apparatus comprises:
    a multi-axial accelerometer configured to be positioned on a body of a person, wherein the multi-axial accelerometer is adapted to generate accelerometer signals indicative of the acceleration along different spatial axes;
    a motion signal generation unit configured to determine weighting factors such that the accelerometer signal having the largest acceleration change has the largest weight at regular time intervals and to linearly interpolate between weighting factors determined at a first time instance and weighting factors determined at a second time instance and to weight the acceleration signals with the weighting factors and to linearly combine the weighted accelerometer signals of different spatial axes to generate a motion signal indicative of heart activity of the person; and
    a heart rate determination unit configured to determine a heart rate depending on the generated motion signal.

8. The motion determination method as defined in claim 5, wherein the determining includes:
    projecting a movement of the gravity vector relative to the spatial axis of the accelerometer on a subspace defined by the nominal gravity vector and the respective spatial axis of the accelerometer; and transforming the respective axis within the subspace such that a projection of the projected movement of the gravity vector, which has been projected into the subspace, on the transformed respective axis is maximized.

9. The motion determination method as defined in claim 8, wherein the combining includes applying a principal component analysis on the maximized projection signals, wherein the resulting first principal component is the generated motion signal.

10. The motion determination apparatus as defined in claim 1, wherein the at least one computer is configured to display the heart rate on a display.

11. The motion determination apparatus as defined in claim 2, wherein the heart rate determination device is configured to display the heart rate on a display.

12. The motion determination method as defined in claim 5, further comprising displaying the heart rate on a display.

13. A non-transitory computer readable medium carrying program code for causing a processor to perform the method of claim 12.

14. The motion determination apparatus as defined in claim 7, wherein the heart rate determination unit is configured to display the heart rate on a display.

* * * * *